(12) United States Patent
Aubert et al.

(10) Patent No.: US 11,844,154 B2
(45) Date of Patent: Dec. 12, 2023

(54) LAMP FOR PHOTOCHEMICAL REACTOR WITH LIGHT-EMITTING DIODES

(71) Applicant: ARKEMA FRANCE, Colombes (FR)

(72) Inventors: Thierry Aubert, Lacq (FR); Rémi Le Bec, Orthez (FR); Fernand Delgado, Orthez (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 17/760,131

(22) PCT Filed: Feb. 22, 2021

(86) PCT No.: PCT/FR2021/050309
§ 371 (c)(1),
(2) Date: Aug. 4, 2022

(87) PCT Pub. No.: WO2021/165627
PCT Pub. Date: Aug. 26, 2021

(65) Prior Publication Data
US 2023/0099496 A1   Mar. 30, 2023

(30) Foreign Application Priority Data
Feb. 20, 2020 (FR) ...................................... 2001693

(51) Int. Cl.
*H05B 33/02* (2006.01)
*H01L 33/64* (2010.01)

(52) U.S. Cl.
CPC ........... *H05B 33/02* (2013.01); *H01L 33/648* (2013.01)

(58) Field of Classification Search
CPC .................................................. H01L 33/648
USPC ........................................................ 313/483
See application file for complete search history.

(56) References Cited

U.S. PATENT DOCUMENTS

| | | | |
|---|---|---|---|
| 3,681,217 | A | 8/1972 | Lucas et al. |
| 3,734,845 | A | 5/1973 | Bravi et al. |
| 2011/0267805 | A1 | 11/2011 | Hua et al. |
| 2016/0081178 | A1 | 3/2016 | D'onofrio |
| 2017/0305851 | A1 | 10/2017 | Uchiumi et al. |

(Continued)

FOREIGN PATENT DOCUMENTS

| | | |
|---|---|---|
| EP | 2868655 A1 | 5/2015 |
| FR | 1331478 A | 7/1963 |
| FR | 2940679 A1 | 7/2010 |

(Continued)

OTHER PUBLICATIONS

"47 kW LED Lamp tor Photochemical Reaction Processes" Toshiba Review Science and Technology Highlights 2016, p. 47.

(Continued)

*Primary Examiner* — Christopher M Raabe
(74) *Attorney, Agent, or Firm* — Boone IP Law

(57) ABSTRACT

A lamp for a photochemical reactor, including: a support member made of a material having a thermal conductivity greater than or equal to 100W/mK at 20° C. and including at least one channel configured to contain a coolant fluid; at least one printed circuit mounted on the support member; and at least one light-emitting diode mounted on the printed circuit. A photochemical reactor including such a lamp, and a method for preparing a cycloalkanone oxime or a lactam using such a lamp.

19 Claims, 3 Drawing Sheets

(56) References Cited

U.S. PATENT DOCUMENTS

2018/0179148 A1    6/2018  Ito et al.
2019/0040005 A1*  2/2019  Dehn ...................... C07B 43/06

FOREIGN PATENT DOCUMENTS

| | | | |
|---|---|---|---|
| JP | 2010006776 A | * | 1/2010 |
| JP | 2019126768 A | | 8/2019 |
| WO | 2009153470 A1 | | 12/2009 |

OTHER PUBLICATIONS

Cambie, D. et al. "Applications of continuous-flow photochemistry in organic synthesis, material science and water treatment" Chemical Reviews, vol. 116, No. 17, Published: Mar. 3, 2016, 161 pages.
International Search Report (PCT/ISA/210) with English translation and Written Opinion (PCT/ISA/237) dated Apr. 6, 2021, by the European Patent Office as the International Searching Authority for International Application No. PCT/FR2021/050309.

* cited by examiner

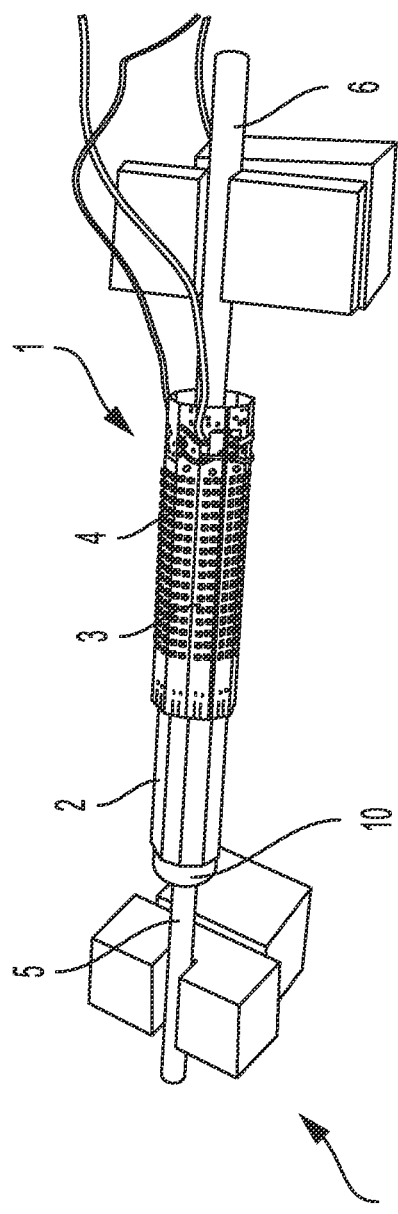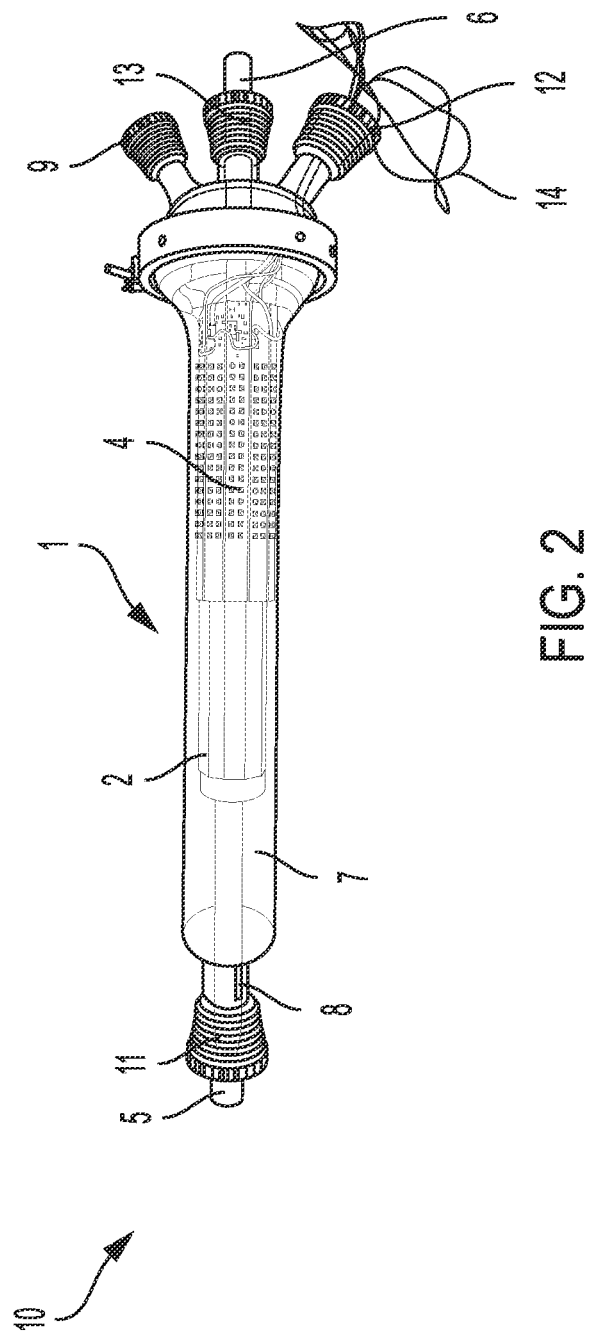

[Fig. 3]
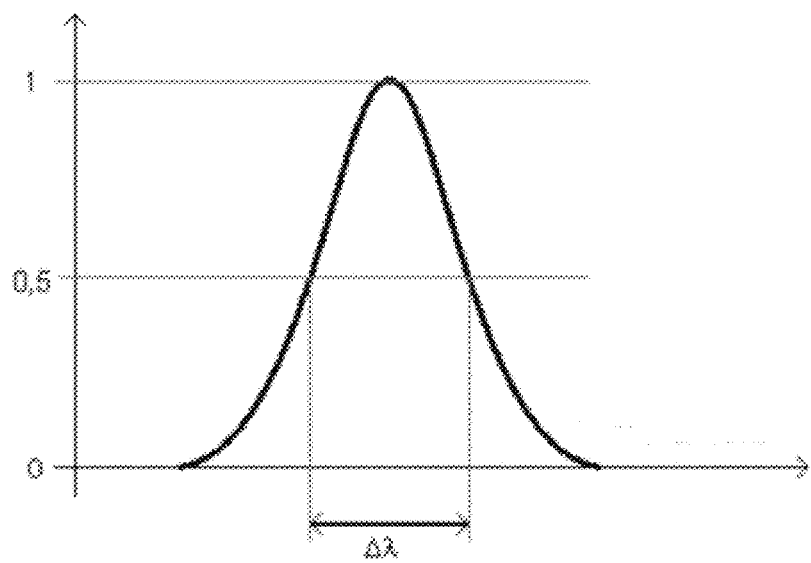
[Fig. 4]
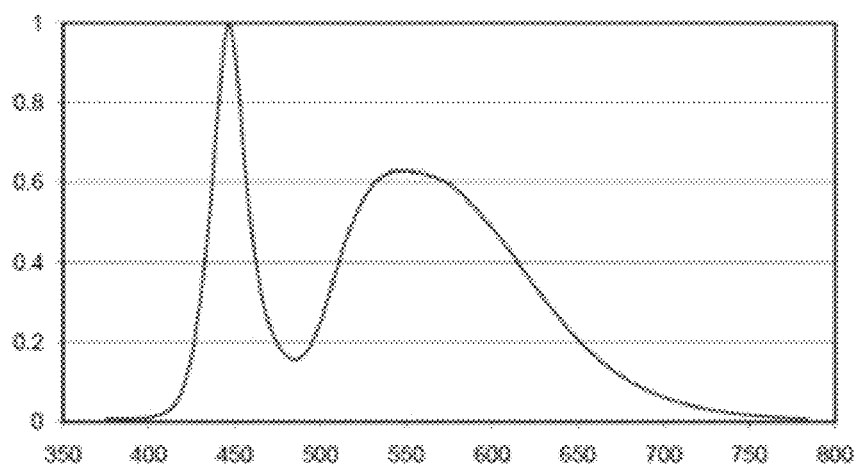

[Fig. 5]
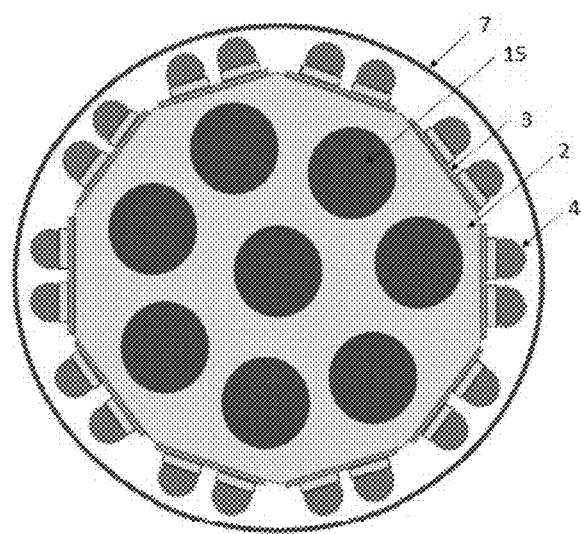

LAMP FOR PHOTOCHEMICAL REACTOR WITH LIGHT-EMITTING DIODES

FIELD OF THE INVENTION

The present invention relates to a lamp for a photochemical reactor, preferably a lamp adapted for an immersion photochemical reactor, comprising at least one light-emitting diode, useful for implementing a photochemical reaction, in particular photonitrozation.

TECHNICAL BACKGROUND

The use of lactams is very common in the industry. Thus, caprolactam and lauryllactam are respectively precursors of polyamides 6 and 12.

On an industrial level, a method for synthesizing a lactam from a cycloalkane can successively implement two reaction steps. In a first reaction step, photonitrozation (or photooximation) of the cycloalkane is completed using, for example, nitrosyl chloride (NOCl), generally in a two-phase organic solvent/sulfuric acid medium. An oxime in the form of oxime hydrochloride is thus produced in an organic phase and is subsequently extracted by the sulfuric phase. In a second reaction step, Beckmann transposition (or Beckmann rearrangement) of the oxime hydrochloride extracted in a concentrated sulfuric medium is completed in order to obtain the lactam. This lactam resulting from the Beckmann transposition is then isolated and purified in order to yield a high-purity product.

Photonitrozation is generally carried out using mercury or sodium vapor lamps immersed in the reaction medium. These sodium or mercury vapor lamps are high electricity consumers. They also have a short service life. Furthermore, they contain a variable amount of mercury and are thus destined to perish in the long run. Replacing these lamps is therefore desirable, preferably without having to significantly modify existing industrial facilities, i.e., using lamps with a footprint similar to that of the sodium or mercury vapor lamps that are currently used.

Light-emitting diodes (or LEDs) have a longer service life than that of sodium or mercury vapor lamps (for example, a mercury vapor lamp can have a service life of the order of 4,000 hrs, a sodium vapor lamp can have a service life of the order of 25,000 hrs, and a light-emitting diode can have a service life of the order of 50,000 to 100,000 hrs). However, since light-emitting diodes do not emit infrared radiation, the heat produced when they are used is only discharged via their power supply, which is disposed on the back of the diodes. Thus, the space that can be used to dissipate the heat that is generated is very limited, in particular when the lamps are immersed in a reaction medium, and light-emitting diodes are therefore more difficult to cool than sodium or mercury vapor lamps, which emit heat in the form of infrared radiation and which can be easily cooled by circulating a coolant fluid around them.

Document WO 2009/153470 relates to a method for preparing lactams, in which the photonitrozation step is completed using light-emitting diodes emitting monochromatic light.

Document US 2018/0179148 describes a power supply system, which in particular allows an increase in temperature of light-emitting diodes to be controlled and which is based on water cooling. The system described in this document has a complicated structure, which appears to be difficult to assemble.

Document US 2017/0305851 describes a photoirradiation device, in which a body comprising a host of light-emitting diodes is placed in two transparent containers, the first container containing a gas and the second container containing a liquid.

Document JP 2019/126768 describes a photoreaction device comprising two groups of diodes that are turned on and off independently and are separated either by an opaque wall or by a light-absorbing substance, so that the radiation from the turned-on diodes does not reach the turned-off diodes.

The document entitled "47 kW LED Lamp for Photochemical Reaction Processes", Toshiba review Science and Technology Highlights 2016, page 47, mentions an LED lamp for photoreaction methods in which the diodes are cooled using water channels. With 70% of the supplied energy being converted into heat, this lamp has 30% luminous efficiency.

A requirement exists for providing a lamp with low power consumption, good luminous power and high luminous efficiency, which can be used in corrosive media such as photonitrozation media, is economical, cost-effective and relatively simple to manufacture.

SUMMARY OF THE INVENTION

The invention firstly relates to a lamp for a photochemical reactor comprising:
- a support made of a material having thermal conductivity that is greater than or equal to 100 W/m·K at 20° C. and comprising at least one channel configured to contain a coolant fluid;
- at least one printed circuit board mounted on said support; and
- at least one light-emitting diode mounted on said printed circuit board.

In embodiments, the material of the support is selected from the group consisting of copper, silver, gold, aluminum, silicon carbide, graphite, aluminum-silicon carbide alloys, zinc, and combinations thereof.

In embodiments, the material of the support has thermal conductivity that is greater than or equal to 300 W/m·K at 20° C.

In embodiments, the lamp further comprises a bulb containing the support, the at least one printed circuit board and the at least one light-emitting diode.

In embodiments, the bulb contains an inert fluid, preferably dinitrogen, the inert gas preferably being in the form of a flow of inert fluid.

In embodiments, the support has a convex polygon-shaped cross-section.

In embodiments, the convex polygon has from 5 to 25 sides.

In embodiments, the at least one channel comprises a coolant fluid, preferably water.

In embodiments, the lamp further comprises a coolant fluid supply line comprising a coolant fluid having a temperature that is less than or equal to 25° C., preferably less than or equal to 10° C., more preferably less than or equal to 5° C.

In embodiments, the lamp has luminous efficiency that is greater than or equal to 40%.

The invention also relates to an immersion photochemical reactor comprising a reaction liquid and at least one lamp as described above at least partially immersed in said reaction liquid.

The invention also relates to a method for preparing a cycloalkanone oxime comprising photonitrozation of a cycloalkane using a nitrozating agent and at least one lamp as described above.

The invention also relates to a method for preparing a lactam comprising:

preparing a cycloalkanone oxime according to the method described above;

Beckmann transposition of the cycloalkanone oxime.

The present invention addresses the aforementioned requirement. More specifically, it provides a lamp with one or more advantageous properties, preferably all these properties, including: improved luminous efficiency, allowing reduced electricity consumption; good luminous power, allowing, when the lamp is used for a photochemical reaction (for example, photonitrozation), high productivity thereof; a long service life; a relatively low cost and good cost-effectiveness. Furthermore, the lamp according to the invention can be compatible with existing facilities using sodium or mercury vapor lamps and can be used in these facilities without or with very few modifications thereto. Moreover, it does not require a complicated design and can be manufactured in a relatively simple manner.

This is accomplished by assembling the one or more light-emitting diodes and the one or more printed circuit boards on a support made of a material with high thermal conductivity, in which at least one channel is present that allows the passage of a coolant fluid. This particular assembly allows very good cooling to be provided both for the light-emitting diodes and the printed circuit boards. Indeed, the coolant liquid is in contact, over a large surface area, with the material of the support with high thermal conductivity, which allows efficient heat exchange to be provided.

According to some particular embodiments, the invention also has the advantage of being able to be used in a corrosive and/or humid medium, such as the reaction medium for the photonitrozation of cycloalkanes.

BRIEF DESCRIPTION OF THE FIGURES

FIG. 1 shows a picture of an example of a lamp according to the invention.

FIG. 2 shows a picture of another example of a lamp according to the invention.

FIG. 3 shows the spectrum of a light-emitting diode. The wavelength is shown on the abscissa and the relative light intensity (i.e., the light intensity divided by the maximum light intensity) is shown on the ordinate. This spectrum shows the mid-height spectral width AA, corresponding to the wavelengths for which the relative light intensity is greater than or equal to 0.5.

FIG. 4 shows the average spectrum of the wavelengths emitted by a white light-emitting diode.

FIG. 5 shows the cross-section of the lamps exemplified according to the embodiment in which there are several channels.

DETAILED DESCRIPTION

The invention is now described in greater detail and in a non-limiting manner in the following description.

Lamp

The invention relates to a lamp, preferably a lamp for a reactor. The reactor can be, for example, any photochemical reaction reactor (also called "photochemical reactor"), preferably it is a photonitrozation reactor.

Preferably, the lamp is configured to be used in an immersion reactor. An "immersion reactor" is understood to mean a reactor in which the light source required for the reaction, i.e., the lamp, is inside the reactor, at least partially immersed in the reaction medium.

The lamp according to the invention comprises a support. This support is made of a material with thermal conductivity that is greater than or equal to 100 W/m·K at 20° C. The thermal conductivity can be measured in accordance with the guarded hot plate method, in accordance with standard ISO 8302.

Examples of materials adapted for the support according to the invention are presented in the following table.

TABLE 1

| Material | Thermal conductivity at 20° C. (W/m · K) |
|---|---|
| copper | 390 |
| aluminum | 237 |
| silicon carbide (SiC) | 350 (for pure SiC) |
| silver | 418 |
| gold | 317 |
| aluminum-silicon carbide (AlSiC) alloys | from 150 to 200 (for alloys with 30 to 60% of SiC) |
| zinc | 116 |
| graphite | up to 1950 |

The material of the support can comprise or consist of the following materials.

The material of the support can also comprise or consist of a combination of two or more of the above materials.

The material of the support can have thermal conductivity that is greater than or equal to 150 W/m·K, or is greater than or equal to 200 W/m·K, or is greater than or equal to 250 W/m·K, or is greater than or equal to 300 W/m·K, or is greater than or equal to 350 W/m·K, or is greater than or equal to 380 W/m·K, at 20° C.

In a particularly preferred manner, the support is made of copper.

Typically, the support has an elongated shape. This allows a main direction (longitudinal) and transverse planes perpendicular to the longitudinal axis of the support to be defined. Preferably, the one or more printed circuit boards is/are disposed on the lateral surface of the support.

In embodiments, the support comprises a longitudinal axis.

In a particularly advantageous manner, the support has a cross-section in the form of a convex polygon.

In embodiments, the support comprises a longitudinal axis, with the section transverse to the longitudinal axis being a convex polygon section.

A "convex polygon" is a simple polygon (i.e., a polygon in which two non-consecutive sides are not intersecting and two consecutive sides share only one of their vertices) in which any segment joining two vertices of the polygon is included in the whole defined by the polygon. The presence of a support having a cross-section in the form of a convex polygon allows an arrangement of the diodes to be provided that optimizes the direction of the light rays emitted by the diodes. Indeed, when the diodes are disposed as a shape comprising concave parts (for example, as a star shape, such as that of the lamp described in the document entitled "47 kW LED Lamp for Photochemical Reaction Processes", Toshiba review Science and Technology Highlights 2016, page 47), some light rays from the diodes located in these concave parts are emitted toward adjacent diodes (next to or opposite) and not toward the rest of the reaction medium.

The rays of the adjacent diodes in the concave parts are superimposed on each other, resulting in a loss of photons for completing the reaction. By contrast, arranging the diodes as a convex polygon shape allows the orientation of the light rays toward the reaction medium to be improved and allows the superimposition of the luminous fluxes of the diodes to be reduced, in order to make the maximum amount of photons available for the reaction.

The polygon can be regular, or basically regular (i.e., all its sides have the same length, or basically the same length, and all its angles have the same measurement, or basically the same measurement) or can be irregular, preferably it is regular or basically regular. The convex polygon can have 3 or more sides, such as a number of sides ranging from 3 to 50, preferably from 4 to 30, more preferably from 5 to 25. For example, the polygon can have 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25 sides.

The support comprises at least one channel (or duct), preferably the support is traversed by said at least one channel. This channel is intended to contain or receive a coolant fluid, preferably a flow of coolant fluid (i.e., a coolant fluid flowing through said channel).

In a particularly advantageous manner, the at least one channel is basically parallel, or parallel, to the longitudinal axis of the support.

In embodiments, the at least one channel is formed, preferably perforated, in the support.

In embodiments, the support comprises a longitudinal axis and the at least one channel traverses the support along this axis.

The support can comprise a single channel or a plurality of channels. For example, the support can comprise from 2 to 40 channels, such as from 2 to 5 channels, or from 5 to 10 channels, or from 10 to 15 channels, or from 15 to 20 channels, or from 20 to 25 channels, or from 25 to 30 channels, or from 30 to 35 channels, or from 35 to 40 channels.

Advantageously, the one or more channels have a specific surface area that is greater than or equal to 0.5 m$^{-1}$ (m$^2$/m$^3$), preferably greater than or equal to 1 m$^{-1}$, preferably greater than or equal to 5 m$^{-1}$, more preferably greater than or equal to 10 m$^{-1}$, more preferably greater than or equal to 20 m$^{-1}$, more preferably greater than or equal to 50 m$^{-1}$, more preferably greater than or equal to 100 m$^{-1}$, even more preferably greater than or equal to 150 m$^{-1}$. The "specific surface area of the channels" is understood to mean the ratio of the surface area of the inner surface of the channels (defining the contact surface between the inside of the channels and the support) to the apparent volume of the support. Such a specific surface can allow a large contact surface, and therefore a heat exchange surface, to be provided between the coolant fluid and the support, and therefore allow good cooling to be provided for the light-emitting diodes and the printed circuit boards.

The presence of channels directly perforated in the high thermal conductivity material of the support allows a large contact surface (and therefore heat exchange surface) to be provided between the coolant fluid circulating in the channel and the support on which the one or more printed circuit boards and the one or more light-emitting diodes are mounted. This results in improved cooling of the printed circuit boards and light-emitting diodes, thus improving the luminous efficiency of the lamp.

Preferably, the at least one channel comprises a coolant fluid, more preferably the coolant fluid circulates in said channel, even more preferably as a continuous flow. The coolant fluid can be any gaseous or liquid fluid known to a person skilled in the art. Preferably, the coolant fluid is a liquid. It can be selected from the group consisting of air, water, aqueous mixtures such as brines (aqueous solutions of calcium and/or sodium chloride), glycated water (water-monoethylene glycol or polypropylene glycol mixtures), mixtures based on alcohol (in particular methanol), ammoniacal water (water-ammonia aqueous solutions), organic fluids such as aliphatic or aromatic hydrocarbons and diphasic coolant fluids such as, for example, liquid-vapor two-phase carbon dioxide or ice slurry consisting of a liquid phase (typically water-alcohol) and ice crystals. Preferably, the coolant fluid is an aqueous solution, more preferably water. The coolant fluid optionally can comprise one or more additives, such as an anti-corrosion agent, an anti-bacterial agent, an algae agent, an antioxidant, etc.

Advantageously, the temperature of the fluid supplied to the support is less than or equal to 25° C. This temperature corresponds to the temperature of the fluid before it has exchanged heat with the support (i.e., at the temperature of the fluid at the inlet of the support). More preferably, the temperature of the fluid at the inlet of the support is less than or equal to 20° C., more preferably less than or equal to 15° C., more preferably less than or equal to 10° C., more preferably less than or equal to 5° C. The temperature of the fluid at the inlet of the support can be, for example, from 0.5 to 5° C., or from 5 to 10° C., or from 10 to 15° C., or from 15 to 20° C., or from 20 to 25° C.

The lamp can comprise a supply line for supplying the coolant fluid to the channel or channels present in the support. Preferably, this supply line comprises coolant fluid. In the supply line, the coolant fluid advantageously has a temperature as described above. The supply line can comprise or be made of one or more materials as described above in relation to the support. For example, the supply line can be made of copper. The one or more materials of the supply line can be identical or different from that or those of the support.

The supply line can be connected to the support via a fluid dispenser, which dispenses the fluid, preferably homogeneously, between the various channels. This dispenser is assembled with the supply line and with the support using all known conventional means, such as soldering, splicing, crimping, etc., depending on the nature of the materials of the assembled elements. For example, if the supply line is made of copper and the support is made of copper, soldering is preferably selected as an assembly means.

The lamp can also comprise a coolant fluid collection line for recovering the coolant fluid after it has passed through the support. The collection line can comprise or be made of one or more materials as described above with respect to the support. For example, the collection line can be made of copper. The one or more materials of the collection line can be identical or different from that or those of the support, and identical or different from that or those of the supply line.

The collection line can be connected to the support via a fluid manifold, which gathers fluids originating from the various channels of the support and directs them to the collection line. This manifold is assembled with the collection line and with the support using any known conventional means such as soldering, splicing, crimping, etc., depending on the nature of the materials of the assembled elements. For example, if the collection line is made of copper and the support is made of copper, soldering is preferably selected as an assembly means.

The coolant fluid can be recycled and reused as a coolant fluid, preferably after cooling, for example, after passing through a heat exchanger.

The lamp comprises at least one printed circuit board (or PCB) mounted on the support.

The at least one printed circuit board can be fixed directly to the support (i.e., directly in contact with the support) or one or more intermediate parts or layers can be present between the circuit and the support, provided that said intermediate parts or layers have good thermal conductivity, for example, greater than or equal to 0.4 W/m·K at 20° C. (as measured, for example, according to standard ISO 8302 using the guarded hot plate method). The circuit can be mounted on the support using any compatible fixing means. Fixing means adapted for mounting the printed circuit board on the support are an adhesive tape, in particular a double-sided adhesive tape, glue, preferably heat conducting glue, screws, clips, or combinations thereof. When the circuit is fixed to the support by means of a double-sided adhesive tape, said tape advantageously has good thermal conductivity, for example, greater than or equal to 0.4 W/m·K at 20° C. (as measured, for example, according to standard ISO 8302 using the guarded hot plate method). When the circuit is fixed to the support by means of glue, said glue advantageously has good thermal conductivity, for example, greater than or equal to 0.4 W/m. K at 20° C. (as measured, for example, according to standard ISO 8302 using the guarded hot plate method).

The PCB can be selected from among all the types of printed circuit board that are known to a person skilled in the art, in particular conventional metal core printed circuit boards ("Metal Core PCB" or MCPCB) (referred to as "Non-direct thermal path" technology) i.e., with a dielectric layer between the LED mounted on the circuit and the metal base of the circuit, or metal core printed circuit boards with "direct thermal path" technology, such as, for example, SinkPAD™ PCBs or TPAD PCBs, i.e., without a dielectric layer between the LED mounted on the circuit and the metal base of the circuit, thereby improving the heat transfer between the LED and the support of the lamp.

In embodiments, the printed circuit boards are disposed on all or part of at least one external face of the support.

In embodiments, the printed circuit boards are disposed on all or part of all the external faces of the support.

The lamp according to the invention comprises at least one light-emitting diode.

Preferably, the light-emitting diode is mounted on the printed circuit board, more preferably directly on the surface of the circuit. The diode can be mounted on the circuit using the Surface Mount Technology (or SMT) components technique or using Through-Hole Technology (or THT). The light-emitting diode can be mounted on the printed circuit board by brazing, soldering, or combinations thereof. The one or more light-emitting diodes is/are disposed so that their radiation emitting part faces outward (relative to the support).

The lamp according to the invention advantageously contains a plurality of light-emitting diodes, for example, between 50 and 100,000 light-emitting diodes. The number of light-emitting diodes can depend on various parameters, such as the size of the photochemical reactor, the power and the wavelength of the LEDs, the desired productivity of the photochemical reaction, etc.

In embodiments, the light-emitting diodes are disposed on all or part of at least one external face of the support.

In embodiments, the light-emitting diodes are disposed on all or part of all the external faces of the support.

The at least one light-emitting diode preferably emits radiation, called monochromatic radiation (such a diode is also called "monochromatic diode" throughout the remainder of the present description). "Light-emitting diode emitting monochromatic radiation" is understood to mean a light-emitting diode having a narrow half-height spectral width (corresponding to the wavelength range with a luminous intensity that is greater than or equal to half the maximum luminous intensity of the spectrum of the diode, as illustrated in FIG. 3), typically a half-height spectral width of 20 to 90 nm, more preferably 20 to 40 nm.

A "dominant wavelength" also can be defined for the LED as being the wavelength perceived by the human eye in the CIE 1931 chromaticity diagram. In the case of monochromatic LEDs, which mostly have a fairly thin emission spectrum, it generally only differs from a few nm of the "peak wavelength" (λpeak) corresponding to the wavelength with the maximum relative energy flux.

Examples of monochromatic LEDs that can be used within the scope of the invention are indicated in the following table:

TABLE 2

| Diode color | Dominant wavelength (nm) |
| --- | --- |
| UV | between 365 and 405 |
| Blue | between 430 and 470 |
| Green | between 525 and 565 |
| Yellow | between 585 and 590 |
| Orange | between 600 and 620 |
| Red | between 625 and 655 |

It is also possible to contemplate, within the scope of the invention, the use of "white" LEDs, the average spectrum of which is illustrated in FIG. 4, which may or may not be associated with light filters for absorbing part of the light spectrum, for example, as a function of the contemplated photochemical reaction.

A very large number of photochemical reactions are known to a person skilled in the art and the wavelengths required to perform them vary over a wide range ranging from the UV to the visible range, as a function of the absorption spectrum of the photoactive species. Numerous examples of photochemical reactions using LEDs have already been described (as, for example, in the article by Cambié et al., "Applications of Continuous-Flow Photochemistry in Organic Synthesis", Material Science, and Water Treatment, Chem. Rev., 2016, 116, 10276-10341) and all the monochromatic or white LEDs described above can be used to complete these reactions.

More preferably, and in particular in the case of a photonitrozation reactor using nitrosyl chloride as a nitrozating agent, the monochromatic radiation emitted by the at least one light-emitting diode has a dominant wavelength ranging from 550 to 750 nm, more preferably from 580 to 740 nm, and even more preferably from 610 to 670 nm, for example, from approximately 550 to 560 nm, or from 560 to 570 nm, or from 570 to 580 nm, or from 580 to 590 nm, or from 585 to 595 nm, or from 590 to 600 nm, or from 600 to 610 nm, or from 610 to 620 nm, or from 620 to 630 nm, or from 630 to 640 nm, or from 650 to 670 nm, or from 670 to 700 nm, or from 700 to 720 nm, or from 720 to 740 nm, or from 740 to 750 nm.

When the lamp according to the invention comprises more than one light-emitting diode, the light-emitting diodes can be identical or different (for example, they can emit at different dominant wavelengths), and are preferably identical. When the light-emitting diodes emit at different dominant lengths, they can all independently emit monochromatic radiation with a dominant wavelength included within the aforementioned ranges.

The lamp according to the invention advantageously comprises a bulb containing the support, the at least one printed circuit board and the at least one light-emitting diode. A "bulb" is understood to mean a gas-tight container. Within the scope of the present invention, the bulb surrounds the assembly formed by the support, the at least one printed circuit board and the at least one light-emitting diode, in other words, this assembly is positioned inside the bulb. The bulb is at least partially transparent (for example, over a surface area corresponding to at least 50%, or at least 80%, of the surface area of the bulb, preferably over the entirety) and, in particular, allows the radiation emitted by the light-emitting diodes to pass over at least part of its surface area (for example, over a surface area corresponding to at least 50%, or to at least 80%, of its surface area, preferably over its entire surface area).

Preferably, the bulb comprises at least one fluid inlet for supplying the bulb with an inert fluid. This fluid inlet can be an opening for a supply line for an inert fluid. More preferably, it comprises at least one fluid outlet, intended for recovering the inert fluid. This fluid outlet can be an opening for a collection line for the inert fluid. Advantageously, (and preferably in addition to the fluid inlet and outlet defined above), the bulb comprises an opening for the passage of the supply line of the coolant fluid and/or an opening for the passage of the collection line of the coolant fluid and/or an opening for the passage of the power supply cables of the light-emitting diodes. In embodiments, the bulb can also comprise a single opening and/or two openings for the passage of the supply and collection lines for all the fluids and electrical cables.

The bulb is advantageously made of glass, for example, borosilicate glass, soda-lime glass and/or lead glass. Alternatively, or additionally, it can be made of acrylic resin, methacrylic resin (PMMA), polystyrene (PS), polyvinyl chloride (PVC), polyester or copolyester, polycarbonate (PC), polyethylene terephthalate (PET), styrene-acrylonitrile copolymer (SAN), and/or any material transparent to the wavelengths emitted by the light-emitting diodes.

The bulb preferably contains an inert fluid. More preferably, the inert fluid is in the form of an inert fluid flow (i.e., the inert fluid circulates through the bulb, entering via the fluid inlet of the bulb and exiting via the fluid outlet of the bulb), more preferably in the form of a continuous flow. An "inert fluid" is understood to mean a fluid incapable of reacting with the reagents present in the reactor.

The inert fluid is preferably an inert gas. The inert fluid can be selected from the group consisting of dinitrogen, helium, neon, argon, krypton and/or xenon. In a particularly preferred manner, the inert fluid is dinitrogen.

The presence of a bulb containing an inert fluid around the entire support, the at least one printed circuit board and the at least one light-emitting diode allows this assembly to be protected and in particular allows the corrosion of the support, of the diode and/or of the circuit to be reduced, or even avoided when the lamp can be subjected to a corrosive atmosphere (such as that of the photonitrozation reaction medium of a cycloalkane, which can contain, for example, nitrosyl chloride, hydrochloric acid, nitrogen oxides and/or water). This protection therefore allows the service life of the lamp to be extended.

The lamp according to the invention advantageously has luminous efficiency that is greater than or equal to 30%. The luminous efficiency, expressed as a percentage, corresponds to the ratio of the luminous power emitted by the lamp (in Watts) to the supplied electric power (or power supply) (in Watts), multiplied by 100. The luminous power emitted by the lamp can be measured by radiometry, for example, using an integrating sphere, in accordance with standard CIE 127 ("Measurement of LEDs"), for example. More preferably, the lamp has luminous efficiency that is greater than or equal to 32%, more preferably greater than or equal to 35%, even more preferably greater than or equal to 38%, even more preferably greater than or equal to 40%.

Photonitrozation Reactor

The invention also relates to a reactor comprising at least one lamp as described above. Preferably, the reactor is an immersion reactor. Advantageously, the lamp is positioned at the center of the reactor. In the event that there is more than one lamp, the lamps are preferably evenly positioned in the volume of the reactor.

Preferably, the reactor comprises a reaction medium, more preferably a reaction liquid. The at least one lamp is preferably partly immersed in said reaction liquid, and more preferably, is completely immersed in said reaction liquid, more preferably without being in contact therewith, for example, by virtue of the presence of hollow cylinders immersed in the reaction medium, in which the at least one lamp is positioned.

Preferably, the reaction medium comprises at least one cycloalkane, advantageously cyclohexane and/or cyclododecane. The reaction medium can also comprise nitrosyl chloride and/or any other nitrozating agent such as, for example, nitrosyl acid sulfate, trichloronitrosomethane or the mixture of chlorine/nitrogen monoxide; furthermore, the reaction medium can comprise sulfuric acid and/or hydrochloric acid and/or water and/or at least one cycloalkanone oxime (preferably cyclododecanone oxime and/or cyclohexanone oxime) and/or a reaction solvent, preferably inert to light and not reactive with the nitrozating agent and the acids present, such as halogenated hydrocarbons such as, for example, halogenomethanes, preferably chloroform and carbon tetrachloride, and/or aromatic hydrocarbons such as, for example, benzene and its halogenated derivatives, and/or alkyl- or aryl-nitriles such as, for example, acetonitrile or benzonitrile.

The reactor according to the invention, in particular for photonitrozation reaction, can comprise a body comprising, or consisting of, PVC, PVDF (polyvinylidene fluoride), glass steel and/or glass. The glasses that can be used for manufacturing the reactor are all types of glass such as borosilicate glasses (Pyrex®, for example), soda-lime glasses, lead glasses, silica glasses and/or glass-ceramics.

Preparation of Cycloalkanone Oximes and/or Lactams and Other Photochemical Reactions The lamp as described above can be used to complete any photochemical reaction such as, for example, photohalogenations, photosulfoxidations, photonitrogenations, photocycloadditions, photocyclizations, photooxygenations, photopolymerizations, photochemical rearrangements, photocatalytic reactions, etc.

Advantageously, the lamp as described above can be used to complete a photonitrozation of a cycloalkane, in particular for preparing a cycloalkanone oxime and/or a lactam.

Photonitrozation of cycloalkane is completed using a nitrozating agent, preferably using nitrosyl chloride (NOCl). A "nitrozating agent" is understood to mean a species or a compound allowing substitution, in a molecule, of a nitrosyl group to a hydrogen atom. Alternatively, or additionally, it can be completed using a gaseous mixture of NOCl and hydrogen chloride, a gaseous mixture of nitrogen monoxide and chlorine, a gaseous mixture of nitrogen monoxide, chlorine and hydrogen chloride, and/or using trichloronitrosomethane (for example, obtained by reacting the NOCl with chloroform) and/or using a mixture capable of forming nitrosyl chloride such as, for example, hydrochloric acid mixed with nitric acid or nitrosyl acid sulfate or alkyl nitrites such as ethyl or amyl nitrite. Photonitrozation is advantageously completed in a two-phase organic solvent/sulfuric acid medium. The temperature and concentration conditions are well known to a person skilled in the art and can be like those described, for example, in documents U.S. Pat. Nos. 3,734,845, 3,681,217 or FR 1331478. An oxime in the form of oxime hydrochloride is thus generated in an organic phase. This oxime then can be extracted by the sulfuric phase.

The cycloalkane is preferably cyclododecane. The cyclododecanone oxime hydrochloride then can be obtained by photonitrozation in accordance with the following reaction:

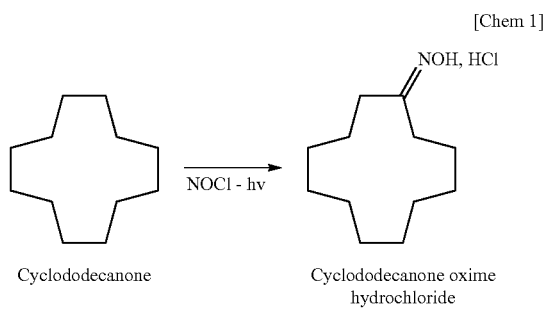

[Chem 1]

Cyclododecane → Cyclododecanone oxime hydrochloride (NOCl - hv, NOH, HCl)

The photon source (hv) is the lamp according to the invention, and more specifically the light-emitting diodes.

Alternatively, or additionally, the cycloalkane can be cyclohexane. The cyclohexanone oxime hydrochloride then can be obtained by photonitrozation The reactor can be a reactor as described above.

A second reaction step then can be completed. Preferably, this second step comprises Beckmann transposition of the oxime derived from the first photonitrozation step. This step is advantageously completed in a concentrated sulfuric medium.

For example, lauryllactam (or dodecalactam) can be obtained from cyclododecanone oxime (which itself is preferably obtained from cyclododecane) in accordance with the following reaction:

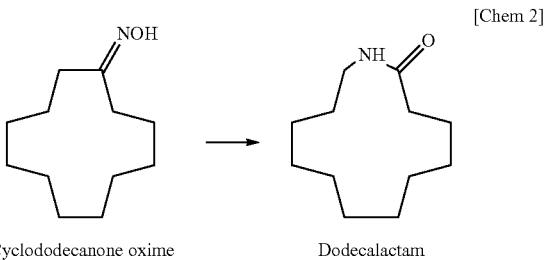

[Chem 2]

Cyclododecanone oxime → Dodecalactam

Caprolactam also can be obtained by Beckmann transposition of cyclohexanone oxime hydrochloride.

Preferably, the Beckmann transposition is completed in a reactor comprising a body comprising glass, preferably a glass body. The use of glass as a material avoids the problems of corrosion that usually arise with conventional materials such as metals. The glasses that can be used for manufacturing the reactor are all types of glass such as borosilicate glasses (Pyrex®, for example), soda-lime glasses, lead glasses, silica glasses and/or glass-ceramics. Alternatively, or additionally, the body of the reactor can comprise, or consist of, tantalum, and/or glassy steel.

Examples

The following examples illustrate the invention yet without limiting the invention.

A control lamp 1 is manufactured.

With reference to FIG. 1, the lamp 1 comprises a copper support 2 with conductivity of 390 W/m·K at 20° C. In this example, the support 2 assumes the shape of a straight prism, is 230 mm long and has a cross-section in the shape of a regular, convex decagon (10-sided polygon). The diameter of the circle circumscribing this decagon is 37.2 mm. The support 2 is traversed, in the longitudinal direction and over its entire length, by 8, 7 mm diameter cylindrical channels 15 (parallel to each other and to the longitudinal axis of the support). One of the channels is positioned at the center of the support and the other 7 are positioned around the central channel, following a circle, and equidistantly relative to each other. The channels 8 are connected, respectively via a fluid dispenser and a fluid manifold 10, to a supply line 6 and a collection line 5, respectively intended for supplying the channels with coolant fluid and for recovering the coolant fluid. At the end of the support 2, on the side of the supply line 6, printed circuit boards 3 are fixed on part of the lateral surface of the support 2, on the 10 sides of the support 2. The printed circuit boards 3 are fixed on the support 2 by means of a double-sided adhesive tape with thermal conductivity of 0.4 W/m·K at 20° C. and the plates of the printed circuit boards are also screwed into the copper support at each of their two ends using two polytetrafluoroethylene screws. Light-emitting diodes 4 with 3.45 mm long sides are soldered onto the printed circuit boards 3 and cover the support 2 over a length of 94 mm. These diodes 4 all have a dominant wavelength of 615 nm. They are available from Cree under reference XPEBRO-L1-0000-00D01 and provide a luminous flux of 107 mA to 350 mA. 32 diodes are disposed on each of the 10 sides of the support, that is 320 LEDs in total.

With reference to FIG. 2, lamp 1 can comprise a glass protective bulb 7. The diameter of the bulb 7 is 44 mm and comprises a fluid inlet 9 and a fluid outlet 8, intended for the circulation of a flow of an inert fluid in said bulb 7. The bulb 7 also comprises an opening 11 for the passage of the collection line 5, an opening 13 for the passage of the supply line 6 and an opening 12 for the passage of the power supply cables 14 of the diodes 4.

The lamp 1 has a 250 W electrical power supply.

The measurement of the luminous flux of the lamp 1 was completed by circulating water at a temperature of 5° C. as a continuous coolant fluid in the supply line 6, then in the channels of the support 2, then in the collection line 5, then by placing the lamp inside a 200 cm integrating sphere by Labsphere, and by measuring the emitted power as a function of the electrical power supply.

The results that were obtained are shown in the following table:

TABLE 3

| Electrical power supply (W) | Emitted luminous power (W) | Luminous efficiency (%) |
|---|---|---|
| 100 | 44.6 | 45 |
| 150 | 63.9 | 43 |
| 200 | 82.3 | 41 |
| 250 | 101.5 | 41 |

The luminous efficiency of the tested lamp 1 therefore ranges between 41 and 45% as a function of the electrical power supply.

The luminous efficiency of a sodium vapor lamp by Philips, reference MASTER SON-T PIA Plus 250 W/220 E40 was determined by measuring the power emitted by the lamp in the same integrating sphere as for the lamp 1. This sodium vapor lamp has a 250 W electrical power supply. It has a 94 mm burner and a 48 mm bulb diameter. This sodium vapor lamp has 36% luminous efficiency.

It therefore can be seen that, with an equal power supply and similar dimensions, the lamp 1 according to the invention has higher luminous efficiency than that of the sodium vapor lamp.

The invention claimed is:

1. A lamp for a photochemical reactor comprising:
a support made of a material having thermal conductivity that is greater than or equal to 100 W/m·K at 20° C. and comprising at least one channel configured to contain a coolant fluid;
at least one printed circuit board mounted on said support; and
at least one light-emitting diode mounted on said printed circuit board.

2. The lamp as claimed in claim 1, wherein the material of the support is selected from the group consisting of copper, silver, gold, aluminum, silicon carbide, graphite, aluminum-silicon carbide alloys, zinc, and combinations thereof.

3. The lamp as claimed in claim 1, wherein the material of the support has thermal conductivity that is greater than or equal to 300 W/m·K at 20° C.

4. The lamp as claimed in claim 1, further comprising a bulb containing the support, the at least one printed circuit board and the at least one light-emitting diode.

5. The lamp as claimed in claim 4, wherein the bulb contains an inert gas, the inert gas being a flow form of inert fluid.

6. The lamp as claimed in claim 1, wherein the support has a convex polygon-shaped cross-section.

7. The lamp as claimed in claim 6, wherein the convex polygon has from 5 to 25 sides.

8. The lamp as claimed in claim 1, wherein the at least one channel comprises the coolant fluid.

9. The lamp as claimed in claim 8, further comprising a coolant fluid supply line comprising the coolant fluid having a temperature that is less than or equal to 25° C.

10. The lamp as claimed in claim 1, having luminous efficiency that is greater than or equal to 40%.

11. An immersion photochemical reactor comprising a reaction liquid and at least one lamp as claimed in claim 1 at least partly immersed in said reaction liquid.

12. A method for preparing a cycloalkanone oxime comprising photonitrozation of a cycloalkane using a nitrozating agent and at least one lamp as claimed in claim 1.

13. A method for preparing a lactam comprising:
preparing a cycloalkanone oxime according to the preparation method of claim 12; and
Beckmann transposition of the cycloalkanone oxime.

14. The lamp as claimed in claim 1, wherein the lamp comprises a coolant fluid supply line is made of copper.

15. The lamp as claimed in claim 1, wherein the lamp comprises a coolant fluid collection line for recovering a coolant fluid after the coolant fluid has passed through the support, the coolant fluid collection line being made of copper.

16. The lamp as claimed in claim 1, wherein the at least one channel configured to contain the coolant fluid is perforated.

17. The lamp as claimed in claim 1, wherein the at least one printed circuit board is a metal core printed circuit board containing a dielectric layer between the at least one light-emitting diode mounted on the at least one printed circuit board and a metal base of the at least one printed circuit board; or is a metal core printed circuit board with direct thermal path technology that does not include a dielectric layer between the at least one light-emitting diode mounted on the at least one printed circuit board and a metal base of the at least one printed circuit board.

18. The lamp as claimed in claim 1, wherein the at least one light-emitting diode is directly mounted onto a surface of the at least one printed circuit board.

19. The lamp as claimed in claim 1, wherein the support comprises from 2 to 40 channels configured to contain the coolant fluid.

* * * * *